(12) United States Patent
Bozzano et al.

(10) Patent No.: US 7,189,885 B1
(45) Date of Patent: Mar. 13, 2007

(54) STAGED PROCESS FOR PRODUCING LINEAR 2-PHENYL-ALKANES

(75) Inventors: Andrea G. Bozzano, Des Plaines, IL (US); R. Joe Lawson, Arlington Heights, IL (US); Paul T. Barger, Arlington Heights, IL (US); Bipin V. Vora, Naperville, IL (US); Kurt A. Detrick, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 466 days.

(21) Appl. No.: 10/680,683

(22) Filed: Oct. 7, 2003

(51) Int. Cl.
*C07C 2/64* (2006.01)
*C07C 2/66* (2006.01)

(52) U.S. Cl. ...................... 585/449; 585/467
(58) Field of Classification Search ............... 585/449, 585/467
See application file for complete search history.

(56) References Cited

U.S. PATENT DOCUMENTS

| | | | | |
|---|---|---|---|---|
| 4,301,317 | A | 11/1981 | Young | 585/455 |
| 4,870,222 | A * | 9/1989 | Bakas et al. | 585/323 |
| 5,196,574 | A | 3/1993 | Kocal | 562/94 |
| 5,276,231 | A | 1/1994 | Kocal et al. | 585/323 |
| 5,302,732 | A | 4/1994 | Steigleder et al. | 554/98 |
| 5,344,997 | A | 9/1994 | Kocal | 568/628 |
| 5,770,782 | A | 6/1998 | Knifton et al. | 585/467 |
| 5,777,187 | A | 7/1998 | Knifton et al. | 585/449 |
| 5,847,254 | A | 12/1998 | Knifton et al. | 585/463 |
| 6,133,492 | A | 10/2000 | Anantaneni | 585/456 |
| 6,166,281 | A | 12/2000 | Anantaneni | 585/449 |
| 6,521,804 | B1 | 2/2003 | Marinangeli et al. | 528/323 |

FOREIGN PATENT DOCUMENTS

| | | |
|---|---|---|
| WO | WO 93/00317 | 7/1993 |
| WO | WO 99/05082 | 2/1999 |
| WO | WO 99/05084 | 2/1999 |
| WO | WO 99/05241 | 2/1999 |
| WO | WO 99/05243 | 2/1999 |
| WO | WO 99/07656 | 2/1999 |
| WO | WO 00/23404 | 4/2000 |
| WO | WO 00/23405 | 4/2000 |
| WO | WO 00/23548 | 4/2000 |
| WO | WO 00/23549 | 4/2000 |

OTHER PUBLICATIONS

*Handbook of Petroleum Refining Processes* edited by Robert A. Meyers, (McGraw-Hill, New York, 2$^{nd}$ Ed., 1997), pp. 1.53 to 1.66 and pp. 5.11 to 5.19.
Meriaudeau P., et al., "Zeolite based catalysts for linear alkylbenzene production: Dehydrogenation of long chain alkanes and benzene alkylation" *Catalysis Today* 38 1997 Elsevier Science B.V. pp. 243-247.
Sivasanker, S. et al., "Distribution of Isomers in the Alkylation of Benzene with Long-Chain Olefins Over Solid Acid Catalysts" *Journal of Catalysis* 138, (1992) pp. 386-390.
Sivasanker, S. et al., "Shape Selective Alkylation of Benzene with Long Chain Alkenes Over Zeolites" *New Frontiers in Catalysis: Proceedings of the 10$^{th}$International Congress on Catalysis*, Jul. 19-24, 1992, Budapest, Hungary, 1993 Elsevier Science Publishers B.V. Editors: L. Guzci et al. pp. 397-408.

* cited by examiner

*Primary Examiner*—Thuan Dinh Dang
(74) *Attorney, Agent, or Firm*—James C. Paschall; Michael A. Moore

(57) ABSTRACT

The process disclosed herein is a process for producing phenyl-alkanes by alkylation of an aryl compound with an olefinic compound and which uses a mordenite catalyst and a silica-alumina catalyst. The selectivity of the process to 2-phenyl-alkanes can be varied over a wide range.

21 Claims, No Drawings

STAGED PROCESS FOR PRODUCING LINEAR 2-PHENYL-ALKANES

FIELD OF THE INVENTION

The invention relates to a process for the selective production of phenyl-alkanes.

BACKGROUND OF THE INVENTION

More than thirty years ago, many household laundry detergents were made of branched alkylbenzene sulfonates (BABS). BABS are manufactured from branched alkylbenzenes (BAB). Then, it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured worldwide.

LABS are manufactured from linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid catalyst. LAB are phenyl-alkanes comprising a linear aliphatic alkyl group and a phenyl group and have the general formula n-phenyl-alkane. In LAB produced using HF catalyst the phenyl group is slightly more likely to attach to a secondary carbon near the center as opposed to near the end of the linear aliphatic alkyl group, and typically only about 18 wt.-% of the n-phenyl-alkanes are 2-phenyl-alkanes. In LAB produced by the Detal™ solid catalyst alkylation process approximately 25–35 wt-% of the n-phenyl-alkanes are 2-phenyl-alkanes. In LAB produced using mordenite catalyst, about 70–80 wt-% of n-phenyl-alkanes are 2-phenyl-alkanes. It is known to produce LAB using both a high-fluorine mordenite-containing catalyst and a silica-alumina catalyst.

The dehydrogenation of linear paraffins to produce linear olefins typically produces aromatic byproducts, as described in U.S. Pat. No. 5,276,231. These aromatics are of the same carbon number as the paraffin being dehydrogenated and may be viewed as aromatized normal paraffins. Typically, the concentration of these aromatic byproducts in the monoolefinic stream is 3–4 wt-%. U.S. Pat. No. 5,276,231 discloses processes for removing these aromatic byproducts.

Processes are sought that produce LAB having practically a range of 2-phenyl-alkane contents.

SUMMARY OF THE INVENTION

In a broad embodiment, this process disclosed herein is a process for the production of LAB by alkylation of an aryl compound with an olefinic compound using a mordenite catalyst and a silica-alumina catalyst, even though the mordenite catalyst contains little or no fluoride, provided that the concentration of aromatic byproducts formed during production of the olefinic compound by paraffin dehydrogenation is kept at a relatively low concentration. By varying the amount of mordenite catalyst upstream of the silica-alumina catalyst, the linear 2-phenyl-alkane content of the LAB can be varied over a wide range.

One embodiment of the process disclosed herein is a process for producing linear alkylbenzenes. Benzene and an olefinic feedstock comprising a linear monoolefin having from about 8 to about 28 carbon atoms and having a concentration of coboiling aromatics of less than 2 wt-% contacts a first catalyst comprising mordenite. The first catalyst operates at first reaction conditions sufficient to alkylate benzene with the monoolefin and form linear phenyl-alkanes. The first catalyst has a fluoride content of less than 0.05 wt-% based on the weight of the mordenite in the first catalyst. A first reaction product comprising linear phenyl-alkanes is recovered from the first reaction zone. At least a portion of the first reaction product is contacted with a second catalyst comprising silica-alumina operating at second reaction conditions. A second reaction product comprising linear phenyl-alkanes is recovered from the process. The linear phenyl-alkanes in the second reaction product comprise linear 2-phenyl-alkane, and the second reaction product has a concentration of linear 2-phenyl-alkanes of from about 25 to about 80 wt-% based on the linear phenyl-alkanes in the second reaction product.

Additional embodiments are described in the following description of this process disclosed herein.

INFORMATION DISCLOSURE

LAB processes are described in the book edited by Robert A. Meyers entitled *Handbook of Petroleum Refining Processes*, (McGraw-Hill, New York, Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

PCT International Publication Nos. WO 99/05082, WO 99/05084, 99/05241, and WO 99/05243, all four of which were published on Feb. 4, 1999, and which are incorporated herein by reference, disclose alkylation processes for uniquely lightly branched or delinearized alkylbenzenes. PCT International Publication No. WO99/07656, published on Feb. 18, 1999, which is incorporated herein by reference, discloses processes for such alkylbenzenes using adsorptive separation.

U.S. Pat. No. 5,196,574 (Kocal) and U.S. Pat. No. 5,344,997 (Kocal) describe alkylation of aromatics using a fluorided silica-alumina catalyst. U.S. Pat. No. 5,302,732 (Steigleder et al.) describes alkylation of aromatics using an ultra-low sodium silica-alumina catalyst. The teachings of U.S. Pat. Nos. 5,196,574, 5,302,732, and 5,344,997 are incorporated herein by reference.

PCT International Publication Nos. WO 00/23548 and WO 00/23549, which were published on Apr. 27, 2000, disclose processes for producing laundry detergents comprising modified alkylbenzene sulfonates and an alkylation step using two or more reactors. These publications state that operating a plurality of reactors allows for material with less preferred 2-methyl-2-phenyl index to be initially formed and to be converted into material with a more preferred 2-methyl-2-phenyl index.

U.S. Pat. No. 4,301,317 discloses reacting aromatic compounds with linear alkylating agents in the presence of mordenite.

U.S. Pat. No. 6,521,804 discloses producing modified alkylbenzenes using a mordenite catalyst and a silica-alumina catalyst.

U.S. Pat. No. 5,777,187 discloses a 2-step process for alkylation of benzene to form linear alkylbenzenes using a fluorine-containing mordenite catalyst and a fluorine containing clay catalyst, such as montmorillonite clay.

PCT International Publication No. WO 00/23404, which was published on Apr. 27, 2000, discloses a process for producing linear alkylbenzene by combining product from a fluorine-containing mordenite catalyst with the feed to a conventional linear alkylbenzene catalyst, such as hydrogen fluoride.

PCT International Publication No. WO 00/23405, which was published on Apr. 27, 2000, discloses a process for producing linear alkylbenzene having a high 2-phenyl isomer content by use of a fluorine-containing mordenite in conjunction with a conventional solid linear alkylbenzene alkylation catalyst, such as silica-alumina (with or without fluorine treatment), clay and aluminum chloride.

The use of mordenite to alkylate benzene with olefins to produce linear alkylbenzenes is described in the articles written by P. Meriaudeau et al., published in Catalysis Today 38 (1997) 243–247, by S. Sivasanker et al., published in Journal of Catalysis 138, 386–390 (1992), and by S. Sivasanker et al., published in New Frontiers in Catalysis, L. Guzci et al. (editors), Proceedings of the 10$^{th}$ International Congress on Catalysis, Jul. 19–24, 1992, Budapest, Hungary, Elsevier Science Publishers B.V. 1993.

U.S. Pat. No. 5,276,231 discloses an alkylaromatic process with removal of diolefins and aromatic byproducts formed during paraffin dehydrogenation.

DETAILED DESCRIPTION OF THE INVENTION

Two feedstocks consumed in the process disclosed herein are an olefinic feedstock comprising an olefinic compound and an aromatic feedstock comprising an aryl compound.

The olefinic feedstock can be entirely linear (unbranched) monoolefins but it is typically a mixture of paraffins and linear (unbranched) monoolefins. All of the monoolefins can have the same number of carbon atoms but they often have from 8 to 15 carbon atoms, and sometimes 10 to 15 carbon atoms. Any paraffins usually have the same number of carbon atoms as the monoolefins.

The olefinic feedstock can be any suitable stream. In one embodiment, the olefinic feedstock can be the paraffin-olefin mixture that is formed as the effluent of a Fischer-Tropsch process. In another embodiment, the olefinic feedstock can be the olefins derived from oligomerization of ethylene, butylene, and/or hexenes. In yet another embodiment, the olefinic feedstock is produced by the following method. First, nonbranched (linear) paraffinic hydrocarbons are separated from a kerosene boiling range petroleum fraction using a process such as the Molex™ process, a commercially proven method for the liquid-phase adsorptive separation of normal paraffins from isoparaffins and cycloparaffins using Sorbex™ separation technology from UOP LLC. See Chapters 10.3 and 10.7 in the book entitled *Handbook of Petroleum Refining Process*, Second Edition, edited by Robert A. Meyers, published by McGraw-Hill, New York, 1997. Then the paraffinic hydrocarbons pass to a dehydrogenation zone, which converts the linear paraffinic hydrocarbons to linear monoolefinic hydrocarbons. The paraffins contact a catalyst, such as those exemplified by U.S. Pat. Nos. 3,274,287; 3,315,007; 3,315,008; 3,745,112; 4,430,517; 4,716,143; 4,762,960; 4,786,625; and 4,827,072. After contacting the catalyst, the effluent is partially condensed, separated from byproduct hydrogen, and further separated to produce a stream containing monoolefinic hydrocarbons and unconverted paraffins. This stream can be used as the olefinic feedstock.

The monoolefinic stream produced by the paraffin dehydrogenation method described above can contain diolefins, which are a common byproduct of the dehydrogenation step. Selective diolefin hydrogenation can be used to convert the diolefins to monoolefins, as described in U.S. Pat. No. 5,276,231, the teachings of which are hereby incorporated herein by reference. In one embodiment, the olefinic feedstock has a concentration of diolefins of less than 0.3 wt-%.

Also, aromatics may be present in the monoolefinic stream formed by the paraffin dehydrogenation method described above, also as a result of side reactions during dehydrogenation processes. These aromatic byproducts are generally of the same carbon number as the paraffins being dehydrogenated, and thus generally of the same carbon number as the product monoolefins. These aromatic byproducts may be viewed as aromatized normal paraffins. Typically, the concentration of these aromatic byproducts in the monoolefinic stream is 3–4 wt-%. This concentration can be decreased by selective removal of these aromatic byproducts, which is also described in U.S. Pat. No. 5,276,231.

Aromatics having the same carbon number as the linear monoolefins in the olefinic feedstock are hereafter referred to herein as "coboiling aromatics." It is an essential feature of one embodiment of the process disclosed herein that the concentration of coboiling aromatics in the olefinic feedstock be less than 2.0 wt-%. This concentration is less than 1.0 wt-% in another embodiment, less than 0.2 wt-% in yet another embodiment, and between 0.1–0.2 wt-% in a fourth embodiment of the process disclosed herein. Without being bound by any particular theory, it is believed the stability of the process disclosed herein is benefited by the combination of a low-fluoride first catalyst and a low concentration of coboiling aromatics in the olefinic feedstock.

The aromatic feedstock comprises an aryl compound, which is benzene when the process is detergent alkylation. In a more general case, the aryl compound of the aromatic feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

In accord with the process disclosed herein, two reaction zones are employed for reacting the olefinic feedstock comprising the monoolefins with the aromatic feedstock comprising the aryl compound.

The first reaction zone contains one or more reactors containing the first catalyst. The feed to the respective reactors of the first reaction zone may contact the respective catalysts in either upflow, downflow, or radial-flow mode. Reactions in the first reaction zone may be conducted either as a batch method or in a continuous manner, although the latter is greatly preferred. The respective catalysts in each of the respective reactors of the first reaction zone may be in a packed bed, a moving bed, or a fluidized bed. The aromatic feedstock or the olefinic feedstock may pass to each respective reactor of the first reaction zone either separately or in an admixture with the other feedstock, or in an admixture with effluent from another reactor of the first reaction zone. The aromatic feedstock may contact the respective catalyst in each of the respective reactors of the first reaction zone in either upflow, downflow, or radial-flow mode. Likewise, the olefinic feedstock to each respective reactor of the first reaction zone may be passed either upflow or downflow, or horizontally as in a radial bed reactor.

The reaction of the aryl compound with the monoolefins in the first reaction zone produces linear n-phenyl-alkanes.

Although the stoichiometry of the reaction in the first reaction zone requires only 1 molar proportion of aryl compound per mole of total monoolefins, the use of a 1:1 mole proportion results in excessive olefin polymerization and can result in polyalkylation. On the other hand, it is desired to have the aryl compound:monoolefin molar ratio as close to 1:1 as possible to maximize utilization of the aryl compound and to minimize the recycle of unreacted aryl compound. The actual molar proportion of aryl compound to total monoolefin will therefore have an important effect on both conversion of the olefinic compound and, perhaps more importantly, selectivity of the alkylation reaction in the first reaction zone. In order to carry out alkylation with the conversion and selectivity required using the catalysts of the process disclosed herein, the total aryl compound: monoolefin molar ratio may be generally from about 1:1 up to about 50:1, more commonly from about 2.5:1 up to about 50:1, and normally from about 8:1 to about 35:1. In one embodiment of the process disclosed herein, the olefinic feedstock may be fed into several discrete points within each respective reactor of the first reaction zone, and at each point the aryl compound:monoolefin molar ratio may be greater than 50:1. However, the total aryl compound:monoolefin ratio used in this embodiment still will be within the stated range.

The reaction conditions of the first reaction zone include a temperature in the range between about 176° F. (80° C.) and about 392° F. (200° C.), most usually at a temperature not exceeding 347° F. (175° C.). Since the alkylation is conducted in at least partial liquid phase, and preferably in either an all-liquid phase or at supercritical conditions, pressures must be sufficient to maintain reactants in the liquid phase. The requisite pressure necessarily depends upon the olefin, the aryl compound, and temperature, but normally is in the range of 100–1000 psi(g) (689–6895 kPa(g)), and most usually 150–500 psi(g) (1034–3448 kPa (g)). The total feed mixture, that is, aromatic feedstock plus olefinic feedstock, passes through the first reaction zone at a liquid hourly space velocity (LHSV) of from about 0.3 to about 1000 hr$^{-1}$ based on the volume of catalyst in the first reaction zone, depending on the desired 2-phenyl-alkane content of the LAB product. As used herein, the abbreviation 'LHSV' means liquid hourly space velocity, which is defined as the volumetric flow rate of liquid per hour divided by the catalyst volume, where the liquid volume and the catalyst volume are in the same volumetric units. The conversion of the olefinic compound in the first reaction zone is less than 50% in one embodiment, less than 10% in another embodiment, and less than 5% in a third embodiment. Olefin conversion in a reaction zone is computed by subtracting the moles of the olefinic compound withdrawn from a reaction zone from the moles of the olefinic compound introduced into the reaction zone, dividing that difference by the moles of the olefinic compound introduced into the reaction zone, and multiplying that quotient by 100.

The catalyst in the first reaction zone, referred to herein as the first catalyst, comprises a zeolite having a MOR zeolite structure type. Such zeolites include mordenite. This zeolite structure type, the term "zeolite structure type," and the term "isotypic framework structure" are used herein as they are defined and used in the *Atlas of Zeolite Structure Types*, by W. M. Meier, et al., published on behalf of the Structure Commission of the International Zeolite Association by Elsevier, Boston, Mass., USA, Fourth Revised Edition, 1996.

It is an essential feature of embodiments of the process disclosed herein that the first catalyst, or the mordenite of the first catalyst, contains less than 0.1 wt-% fluoride, based on the weight of the mordenite in the first catalyst. In other embodiments, the first catalyst, or the mordenite thereof, contains less than 0.05 wt-% fluoride, based on the weight of the mordenite in the first catalyst. In yet other embodiments, the first catalyst, or the mordenite thereof, contains less than 0.01 wt-% fluoride, based on the weight of the mordenite in the first catalyst. In yet another embodiment, the first catalyst or the mordenite thereof contains no fluoride. These very low levels of fluoride on the first catalyst are advantageous. Neither the first catalyst nor the mordenite of the first catalyst need to be treated with a fluoride, typically HF, to add or increase its fluoride content. Low fluoride catalysts can be less expensive because fluoride does not need to be added during catalyst manufacture. Also, costly steps for removing fluoride from the effluent stream and various product streams, including the LAB product, may not be needed.

Useful zeolites for the first catalyst in the process disclosed herein generally have at least 10 percent of the cationic sites thereof occupied by ions other than alkali or alkaline-earth metals. Such other ions include, but are not limited to hydrogen, ammonium, aluminum, rare earth, zinc, copper, and aluminum. Of this group, particular preference is accorded ammonium, hydrogen, rare earth, or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, such as the metals of Groups IIIB (IUPAC 3), IVB (IUPAC 4), VIB (IUPAC 6), VIIB (IUPAC 7), VIII (IUPAC 8–10), and IIB (IUPAC 12). It is also contemplated that the zeolites may, in some instances, desirably be subjected to thermal treatment, including steaming or calcination in air, hydrogen, or an inert gas, e.g. nitrogen or helium. A suitable steaming treatment comprises contacting the zeolite with an atmosphere containing from about 5 to about 100% steam at a temperature of from about 250° C. (482° F.) to 1000° C. (1832° F.). Steaming may last for a period of between about 0.25 and about 100 hours and may be conducted at pressures ranging from sub-atmospheric to several hundred atmospheres.

It may be useful to incorporate the zeolites that are useful in the process disclosed herein in another material, e.g., a matrix material or binder that is resistant to the temperature and other conditions used in the process. Suitable matrix materials include synthetic substances, naturally occurring substances, and inorganic materials such as clay, silica, and/or metal oxides. Matrix materials can be in the form of gels including mixtures of silica and metal oxides. Gels including mixtures of silica and metal oxides may be either naturally occurring or in the form of gels or gelatinous precipitates. Naturally occurring clays which can be composited with the zeolite used in the process disclosed herein include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used as a matrix material in their raw states as originally mined, or can be subjected to calcination, acid treatment or chemical modification prior to their use as matrix materials. In addition to the foregoing materials, the zeolite used in the process disclosed herein may be compounded with a porous matrix material, such as alumina, silica-alumina, silica-magnesia, silica-zirconia, silica-thoria, silica-beryllia, silica-titania, and aluminum phosphate as well as ternary combinations, such as silica-alumina-thoria, silica-alumina-zirconia, silica-alumina-magnesia, and silica-magnesia-zirconia. The matrix material may be in the form of a cogel. The relative proportions of any matrix material may vary widely, with the zeolite content ranging generally from between about 1 and about 99% by weight, usually in the range of about 5 to about 80% by weight, and preferably in the range of about 30 to about 80% by weight, of the combined weight of zeolite and matrix material.

The zeolites that are useful in the alkylation catalyst generally have a framework silica:alumina molar ratio of from about 5:1 to about 100:1. When the zeolite of the alkylation catalyst is mordenite, the mordenite has a framework silica:alumina molar ratio generally of from about 12:1 to about 90:1, and preferably of from about 12:1 to about 25:1. As used herein, the term "framework silica:alumina molar ratio" means the molar ratio of silica per alumina, that is the molar ratio of $SiO_2$ per $Al_2O_3$, in the zeolite framework.

When zeolites have been prepared in the presence of organic cations they may not be sufficiently catalytically active for alkylation. Without being bound to any particular theory, it is believed that the insufficient catalytic activity is the result of the organic cations from the forming solution occupying the intracrystalline free space. Such catalysts may be activated, for example, by heating in an inert atmosphere at 540° C. (1004° F.) for one hour, ion exchanging with ammonium salts, and calcining at 540° C. (1004° F.) or above in air. Preferably, the calcination conditions are sufficient to decompose at least a portion of, and more preferably all of, any ammonia present in the catalyst. The presence of organic cations in the forming solution may be essential to forming particular zeolites. Some natural zeolites may sometimes be converted to zeolites of the desired type by various activation procedures and other treatments such as ion exchange, steaming, alumina extraction, and calcination. When synthesized in the alkali metal form, the zeolite is conveniently converted to the hydrogen form, generally by intermediate formation of the ammonium form as a result of ammonium ion exchange and calcination of the ammonium form to yield the hydrogen form. Although the hydrogen form of the zeolite catalyzes the reaction successfully, the zeolite may also be partly in the alkali metal form.

The first reaction zone produces a first effluent comprising the desired phenyl-alkanes. In addition to phenyl-alkanes, the first effluent may also comprise paraffinic hydrocarbons, monoolefinic hydrocarbons, and polyalkylbenzenes such as phenyl-dialkanes and phenyl-trialkanes, but it is not a requirement of the process disclosed herein that the first effluent comprise any of these additional components. For example, the first effluent stream may contain no monoolefinic hydrocarbons. The effluent of the first reaction zone passes to a second reaction zone.

The second reaction zone contains one or more reactors containing the second catalyst. The feed to the respective reactors may contact the respective catalysts in either upflow, downflow, or radial-flow mode. Reactions in the second reaction zone may be conducted either as a batch method or in a continuous manner, although the latter is greatly preferred. The respective catalysts in each of the respective reactors may be in a packed bed, a moving bed, or a fluidized bed. The first effluent may be passed to each respective reactor either separately or in an admixture with the aromatic feedstock, the olefinic feedstock, or both. However, it is not a requirement of the process disclosed herein that any aromatic feedstock or any olefinic feedstock be passed to the second reaction zone. Indeed, in one embodiment of the process disclosed herein no monoolefin contacts the second catalyst. But if either any aromatic feedstock or any olefinic feedstock passes to any reactor in the second reaction zone, that feedstock may be introduced in either upflow, downflow, or radial-flow mode, and/or may be introduced in an admixture with the other feedstock. If the olefinic feedstock is introduced to any reactor in the second reaction zone, the olefinic feedstock is introduced at a total aryl compound:monoolefin molar ratio of generally from about 1:1 up to about 50:1, and more commonly between 2.5:1 and 50:1, and if fed into several discrete points within the second reaction zone, at each point the aryl compound:monoolefin molar ratio may be greater than 50:1. The relative amounts of olefinic feedstock to each reactor of the first reaction zone, the second reaction zone, or both, can be varied to attain the desired linear 2-phenyl-alkane content of the LAB product.

The second catalyst is a solid catalyst having an acid function, that is a solid acid catalyst. Suitable second catalysts include materials comprising amorphous silica-alumina. A fluorided silica-alumina catalyst, particularly one with a weight ratio of silica to alumina in the range of at least 0.5:1 (33 wt-%) up to as high as 9:1 (90 wt-%) containing from 1 to 6 wt-% fluoride, is particular effectively effective as the second catalyst. See U.S. Pat. Nos. 5,196,574 and 5,344,997, the teachings of which are incorporated herein by reference. The stated silica-alumina weight ratio is a useful compromise between selectivity and activity. Selectivity of processes using the fluorided silica-aluminas of this preferred catalyst increases with increasing silica content, which recommends or suggests the use of as high a silica level as possible. However, the activity of the fluorided materials increases initially, appears to pass through a maximum at about a 3:1 ratio of silica:alumina, and then decreases thereafter. Accordingly, although fluorided silica-aluminas can be used throughout the given range, those having a silica to alumina weight ratio between about 65:35 and 85:15 are preferred for this catalyst. Preferably, this preferred fluorided silica-alumina catalyst contains from about 1 up to 6 weight percent fluoride based on volatile-free finished silica-alumina catalyst. Higher fluoride levels may be used but without any substantial incremental benefit. The preferred fluoride level depends on the silica-alumina ratio. For example, for a 75:25 silica:alumina ratio fluoride levels between about 1.5 and 3.5 are preferred. The second catalysts include silica-aluminas having an ultra-low sodium content of preferably less than about 0.5 weight percent and more preferably less than about 0.1 weight percent. See U.S. Pat. No. 5,302,732, the teachings of which are incorporated herein by reference. In one embodiment, the second catalyst does not contain any fluoride. The silica-aluminas may contain a weight ratio of silica to alumina of at least 1:1 up to as high as 19:1, but a silica:alumina ratio of 2:1 (67/33) up to about 19:1 (ca. 95:5) is preferred. Optionally, after the second catalyst has been prepared as described above, it may hydrated by means known in the art, such as exposing the second catalyst to a water-containing gas. The loss on ignition at 500° C. (932° F.) based on the hydrocarbon-free weight of the second catalyst (hereafter "LOI") of the second catalyst is from about 1 to about 12 wt-% in one embodiment, from about 1 to about 8 wt-% in another embodiment, from about 4 to about 8 wt-% in a third embodiment, from 6 to about 12 wt-% in a fourth embodiment, and from about 1 to about 3 wt-% in a fifth embodiment. A sample of the second catalyst for the LOI analysis may be taken when the second catalyst is loaded into the second reaction zone, during operation (using an on-line catalyst sampler), and when it is unloaded from the second reaction zone.

The effluent of the second reaction zone contains the same kinds of n-phenyl-alkanes described previously as having been produced in the first reaction zone. Based on the phenyl-alkanes in the effluent of the second reaction zone, the 2-phenyl-alkanes comprise from 25 to 80 wt-% in one embodiment, from 35 to 70 wt-% in another embodiment, from 35–45 wt-% in a third embodiment, from 45–55 wt-% in a fourth embodiment, from 55–65 wt-% in a fifth embodiment, and from 65–70 wt-% in a sixth embodiment.

The reaction conditions of the second reaction zone include a temperature of from about 176° F. (80° C.) to about 437° F. (225° C.), usually from about 266° F. (130° C.) to about 347° F. (175° C.), and most usually at a temperature not exceeding 392° F. (200° C.). In one embodiment, the inlet temperature of the olefinic feedstock, the aromatic feedstock, or the combination of the two feedstocks entering the second reaction zone is lower than the temperature of the olefinic feedstock, the aromatic feedstock, or the combination of the two feedstocks entering the first reaction zone. Since the reaction is conducted in at least partial liquid phase, and preferably in either an all-liquid phase or at supercritical conditions, pressures must be sufficient to maintain reactants in the liquid phase. The requisite pressure necessarily depends upon the olefin (if any), the aryl compound (if any), the phenyl-alkanes, and temperature, but normally is in the range of 100–1000 psi(g) (689–6895 kPa(g)), and most usually 150–500 psi(g) (1034–3448 kPa (g)). The total feed mixture, that is, effluent of the first reaction zone plus any aromatic feedstock as well as any olefinic feedstock, passes through the second reaction zone at a liquid hourly space velocity (LHSV) of from about 0.3 to about 20 $hr^{-1}$ based on the volume of catalyst in the first reaction zone, depending on the desired 2-phenyl-alkane content of the LAB product.

The second reaction zone produces a second effluent that enters separation facilities for the recovery of products and recyclable feed compounds. The second effluent stream passes into a column (commonly called a "benzene column," when the aryl compound comprises benzene) which produces an overhead stream containing the aryl compound and a bottoms stream containing the phenyl-alkane product. This bottoms stream passes into a paraffin column which produces an overhead liquid stream containing unreacted paraffins and a bottoms stream containing the product phenyl-alkanes and any higher molecular weight side product hydrocarbons formed in the first or second reaction zones. This paraffin column bottoms stream may pass to a rerun column which produces an overhead alkylate product stream containing the detergent-grade phenyl-alkanes and a rerun column bottoms stream containing polymerized olefins and polyalkylated benzenes (heavy alkylate). Alternatively, if the heavy alkylate content of the paraffin column bottoms stream is sufficiently low, a rerun column is not necessary and the paraffin column bottoms stream may be recovered as the net detergent phenyl-alkanes stream from the process.

It is within the scope of the present process disclosed herein to recycle an aliquot portion of the effluent of the first reaction zone to the first reaction zone, to recycle an aliquot portion of the effluent of the second reaction zone to the first reaction zone, to recycle an aliquot portion of the effluent of the second reaction zone to the second reaction zone, and to recover phenyl-alkane from the process from an aliquot portion of the effluent of the first reaction zone. Each of these may be done alone or in combination with one or more of the others. An aliquot portion of an effluent is a portion that has essentially the same composition as the effluent.

Without limiting the process disclosed herein as set forth in the claims to any particular theory, it is believed that the reaction conditions of the first reaction zone yield a relatively high amount of 2-phenyl-alkanes per phenyl-alkane produced, and the reaction conditions of the second reaction zone yield a relatively low amount of 2-phenyl-alkanes per phenyl-alkane produced. In one embodiment of the process disclosed herein, the catalyst comprising mordenite is in the first reaction zone.

By using different amounts of catalyst in the first reaction zone relative to the total amount of catalyst in both the first and second reaction zones, a desired amount of 2-phenyl-alkanes in the second reaction product can be obtained.

The first catalyst represents about 1% to about 70% by volume of the total volume of catalyst in the two reaction zones. The relative volumes of first and second catalyst depend on product objectives. If the objective is high production of 2-phenyl-alkanes, the first catalyst advantageously comprises a substantial proportion, such as from about 50% to about 60% by volume, of the total volume of catalyst. If the objective is low 2-phenyl-alkanes, the first catalyst comprises a smaller proportion, such as from about 5% to about 15% by volume, of the total volume of catalyst in both the first and second reaction zones. Other possible volume proportions of catalyst in the first reaction zone are from about 5% to about 70%, from about 5% to about 60%, from about 10% to about 50%, and from about 15% to about 40%, of the total volume of catalyst.

Either the first or second catalyst used in the process disclosed herein may become deactivated by byproducts which are preferentially adsorbed by the catalysts. Such byproducts include, for example, polynuclear hydrocarbons in the 10 to 20 carbon atom range formed in the dehydrogenation of $C_6$ to $C_{20}$ linear paraffins and also include products of higher molecular weight than the desired monoalkyl benzenes, e.g., di- and tri-alkyl benzenes, as well as olefin oligomers. Although it can be readily appreciated that such catalyst deactivating agents or "poisons" are an adjunct of aromatic alkylation, fortunately it has been observed that such deactivating agents can be readily desorbed from the first and second catalysts by contacting the catalyst with the aromatic feedstock. In particular, the preferred mordenite, silica-alumina, and fluorided silica-alumina catalysts for use in the process disclosed herein can be reactivated in this manner. Thus, catalyst reactivation, or catalyst regeneration as the term is more commonly employed, is conveniently effected by flushing the catalyst with the aryl compound to remove accumulated poisons from the catalyst surface, generally with restoration of 100% of catalyst activity.

During catalyst regeneration, the catalyst temperature is generally in the range of from about 212° F. (100° C.) to about 752° F. (400° C.) and more typically from about 392° F. (200° C.) to about 572° F. (300° C.). During regeneration the flow rate of the aryl compound is selected to achieve sufficient flushing of poisons from the catalyst. The pressure during regeneration is selected so that the regeneration takes place in a liquid phase in an embodiment of the process disclosed herein, in at least a partial liquid phase in another embodiment, and at supercritical conditions in a yet another embodiment. Both the first and second catalysts can be regenerated at effectively the same time by allowing the aryl compound to pass in a series-flow fashion through one reaction zone and then through the other reaction zone. During regeneration the difference between the temperature of the first catalyst and the temperature of the second catalyst is less than 100° F. (56° C.) in an embodiment, less than 40° F. (22° C.) in a second embodiment, and less than 10° F. (6° C.) in a third embodiment. During regeneration the difference between the pressure of the first catalyst and the pressure of the second catalyst is less than 50 psi (344 kPa) in one of the embodiments of the process disclosed herein, less than 20 psi (138 kPa) in another one of the embodiments, and less than 5 psi (34 kPa) in still another embodiment. During regeneration the difference between the volumetric flow rate of the aryl compound contacting the first catalyst and the volumetric flow rate of the aryl compound contacting the second catalyst is less than 50% in one embodiment, less than 5% in another embodiment, and less than 1% in a third embodiment, of the volumetric flow rate of the aryl compound contacting the first catalyst.

The first or second catalyst may be contained in a fixed-bed reactor, or in a moving-bed reactor or in a fluidized bed reactor whereby catalyst may be continuously withdrawn and added. These alternatives are associated with catalyst regeneration options known to those of ordinary skill in the art, such as: (1) a semiregenerative unit containing fixed-bed reactors maintains operating severity by increasing temperature, eventually shutting the unit down for catalyst regeneration and reactivation; (2) a swing-reactor unit, in which individual fixed-bed reactors containing catalyst that has become deactivated are serially isolated by manifolding arrangements and the catalyst in one or more isolated reactors is regenerated and reactivated while the other reactors remain on-stream; (3) continuous regeneration of catalyst withdrawn from a moving-bed reactor or a fluidized bed reactor, with reactivation and substitution with the reactivated catalyst; or (4) a hybrid system with semiregenerative and continuous-regeneration provisions in the same zone. The preferred embodiment of the process disclosed herein is the fixed-bed reactor in a swing-reactor first reaction zone and a fixed-bed reactor in a swing-reactor second reaction zone.

Each of the first and second reaction zone may comprise a single reactor containing the respective catalyst or, alternatively, two or more parallel reactors with valving as known in the art to permit alternative cyclic regeneration. The choice between a single reactor and parallel cyclical reactors depends inter alia on the reactor volume and the need to maintain a high degree of yield consistency without interruption; preferably, in any case, the reactors of each zone are valved for removal from the process combination so that the respective catalyst may be regenerated or replaced while the other reactor(s) of the zone remain in operation.

In an alternative embodiment, it is within the ambit of the process disclosed herein that each of the two zones, and in particular the first reaction zone, comprises two or more reactors with heat exchange (e.g., heating or cooling) between reactors to lower the temperature and maintain alkylation conditions. This may be advantageous, especially in the first reaction zone, since the major reaction occurring in the first reaction zone is the alkylation of the aryl compound with the olefinic compound, and the resulting exothermic heat of reaction may heat the feedstocks above the temperature at which alkylation takes place in the substantial absence of skeletal isomerization. In another alternative embodiment, reaction temperatures may be maintained in the first or second reaction zone by inclusion of heat-exchange internals in a reactor of the first or second reaction zone. The heat-exchange internals may be bayonet-tubes or elongated compartments alternatively containing catalyst with reactants and a heat carrier fluid. Heat exchange may also be done between the first and second reaction zones.

Sulfonation of the phenyl-alkanes produced by the processes disclosed herein can be accomplished by contacting the phenyl-alkane compounds with any of the well-known sulfonation systems, including those described in *Detergent Manufacture Including Zeolite Builders and Other New Materials*, by Marshall Sittig, Noyes Data Corporation, Park Ridge, N.J., 1979, and in Volume 56 of "Surfactant Science" series, Marcel Dekker, Inc., New York, N.Y., 1996. Sulfonation of the phenyl-alkane compounds produces a sulfonated product comprising phenyl-alkane sulfonic acids. Common sulfonation systems employ sulfonating agents such as sulfuric acid, chlorosulfonic acid, oleum, and sulfur trioxide. Sulfonation using a mixture of sulfur trioxide and air is described in U.S. Pat. No. 3,427,342.

After sulfonation, the sulfonated product can be neutralized by contact with any suitable alkali, such as sodium, potassium, ammonium, magnesium, calcium, and substituted ammonium alkalis, and mixtures thereof. Neutralization of the phenyl-alkane sulfonic acids produces a neutralized product comprising phenyl-alkane sulfonates. Suitable neutralizing agents include sodium hydroxide, potassium hydroxide, ammonium hydroxide, sodium carbonate, sodium bicarbonate, potassium carbonate, magnesium hydroxide, magnesium carbonate, basic magnesium carbonate (magnesia alba), calcium hydroxide, and calcium carbonate, and mixtures thereof.

It is within the scope of the process disclosed herein that the order of the first reaction zone and the second reaction zone is reversed, i.e., an alternative embodiment is reacting the aromatic feedstock and the olefinic feedstock with a silica-alumina catalyst to obtain a phenyl-alkane effluent which is processed in a reaction zone containing a mordenite catalyst to obtain a phenyl-alkane product. Operating conditions, catalysts, and relative volumes of the two catalysts for the two zones in this embodiment are within the parameters described above.

It is also within the scope of the process disclosed herein that a single reaction zone contains a physical mixture of the previously described first and second catalysts. Operating conditions, catalysts, and relative volumes of the first and second catalysts for the reaction zone of this embodiment are within the parameters described above.

The following examples are solely for purposes of illustration. These examples show in detail how the process disclosed herein claimed below may be effected, and are not meant to limit the scope of the process disclosed herein to the embodiments shown in the examples. These examples are not meant to limit the scope of the process disclosed herein as set forth in the claims.

EXAMPLE 1

Example 1 illustrates preparation of a mordenite-containing alkylation catalyst for use in the process disclosed herein that was formulated by a method consistent with that of an alkylation catalyst. The starting material for the mordenite-containing catalyst was the hydrogen form of a mordenite having a molar ratio of silica:alumina of 18, hereinafter referred to as the starting mordenite. 50 parts by weight of the starting mordenite were mixed with 50 parts by weight of alumina powder. An acidified peptization solution was added to the mixture. The admixture was then extruded by means known in the art. After the extrusion process, the extrudate was dried and calcined at a temperature of 538° C. (1000° F.). The fluoride contents of the catalyst and of the mordenite in the catalyst were less than 0.05 wt-%, based on the weight of the mordenite in the catalyst. The catalyst prepared in this example is referred to as catalyst A.

EXAMPLE 2

Example 2 illustrates preparation of a fluorided silica-alumina catalyst for use in the process disclosed herein. The fluorided silica-alumina catalyst was prepared in a manner substantially similar to that described in U.S. Pat. No. 5,344,997. The weight ratio of silica per alumina, that is the weight ratio of $SiO_2$ per $Al_2O_3$, was 3:1, the fluoride content was 2.8 wt-% based on the volatile-free finished silica-alumina catalyst. Two catalysts were prepared with this method at different times and using equipment of different scales. These are referred to as catalysts B and C.

EXAMPLE 3

Quantities of catalysts B and C were hydrated at different times and using equipment of different scales until the LOI of each catalyst was between 6 and 8 wt-%. The hydrated catalyst B is referred to as catalyst D, and the hydrated catalyst C is referred to as catalyst E.

EXAMPLE 4

A sample of an olefinic feedstock containing olefins and paraffins from a commercial LAB process was obtained. The olefinic feedstock was formed by dehydrogenation of paraffins with subsequent removal of aromatic byproducts and contained less than 0.2 wt-% coboiling aromatics. The distribution of olefins in the olefinic feedstock was as shown in Table 1.

TABLE 1

Distribution of Olefins in Olefinic Feedstock

| Olefin Component | Content (wt-%) |
|---|---|
| Lights[1] | <1 |
| Normal decene | 13 |
| Normal undecene | 32 |
| Normal dodecene | 31 |
| Normal tridecene | 24 |
| $C_{14}$+ olefins | <1 |
| Heavies[2] | |
| Others[3] | <1 |
| Total | 100 |

[1]Lights include olefins having fewer than 10 carbon atoms.
[2]Heavies include olefin dimers and trimers.
[3]Other alkyl olefins include dimethyl, trimethyl, and other olefins The sample was mixed with benzene to produce a combined feedstock consisting of 60 wt-% benzene and 4.0 wt-% normal olefins. A cylindrical reactor with an inside diameter of 0.5 in (12.7 mm) was loaded with a volume of catalyst B.

The reactor was then subjected to a 24-hour alkylation test using the combined feedstock. The test was carried out at a LHSV of 10 $hr^{-1}$ based on the flow rate of the combined feedstock and the volume of catalyst B in the reactor. The test was carried out at a temperature of 140° C. (284° F.) and a pressure of 3447 kPa(g) (500 psi(g)). The reactor effluent was collected and analyzed at 4-hour intervals during the 24 hour test.

EXAMPLE 5

An alkylation test was conducted as in Example 4, except that the reactor was loaded with a volume of catalyst A and a volume of catalyst B. Catalyst A was loaded near the reactor inlet for the combined feedstock and catalyst B was loaded near the outlet for the reactor effluent, so that the hydrocarbon contacted catalyst A first and then catalyst B. The total volume of catalysts A and B was the same as that of catalyst A in Example 4. The LHSV was 10 $hr^{-1}$ based on the flow rate of the combined feedstock and the total volume of catalysts A and B in the reactor. The volume of catalyst A was 15% (by volume) of the total volume of catalysts A and B.

EXAMPLE 6

An alkylation test was conducted as in Example 4, except the reactor was loaded with a volume of a mixture of catalysts A and B. The mixture was prepared by adding 15 parts by volume of catalyst A and 85 parts by volume of catalyst B into a container and then agitating the container to commingle the two catalysts. The volume of the mixture was the same as that of catalyst A in Example 4. The LHSV was 10 $hr^{-1}$ based on the flow rate of the combined feedstock and the volume of the catalyst mixture.

EXAMPLE 7A

An alkylation test was conducted as in Example 4, except the reactor was loaded with a volume of catalyst E and the test was carried out with a LHSV of 3.75 $hr^{-1}$ based on the flow rate of the combined feedstock and the volume of catalyst E in the reactor.

EXAMPLE 7B

This is a prophetic example. An alkylation test is conducted as in Example 7A, except the reactor is loaded with a volume of catalyst D. The volume of catalyst D is the same as the volume of catalyst E in Example 7A. The test is carried out with a LHSV of 3.75 $hr^{-1}$ based on the flow rate of the combined feedstock and the volume of catalyst D in the reactor. The 2-phenyl content of the LAB product is essentially the same as the 2-phenyl content of the LAB product in Example 7A.

EXAMPLE 8

An alkylation test was conducted as in Example 7A, except that the reactor was loaded with a volume of catalyst A and a volume of catalyst D. Catalyst A was loaded near the reactor inlet for the combined feedstock and catalyst D was loaded near the outlet for the reactor effluent, so that the hydrocarbon contacted catalyst A first and then catalyst D. The total volume of catalysts A and D was the same as that of catalyst E in Example 7A. The LHSV was 3.75 $hr^{-1}$ based on the flow rate of the combined feedstock and the total volume of catalysts A and D in the reactor. The volume of catalyst A was 5% (by volume) of the total volume of catalysts A and D.

EXAMPLE 9

An alkylation test was conducted as in Example 4, except that the reactor was loaded with a volume of catalyst C. The volume of catalyst C was the same as that of catalyst A in Example 4. The LHSV was 10 hr$^{-1}$ based on the flow rate of the combined feedstock and the volume of catalyst C.

EXAMPLE 10

An alkylation test was conducted as in Example 9, except that the reactor was loaded with a volume of catalyst C and a volume of catalyst A. Catalyst C was loaded near the reactor inlet for the combined feedstock and catalyst A was loaded near the outlet for the reactor effluent, so that the hydrocarbon contacted catalyst C first and then catalyst A. The total volume of catalysts C and A was the same as that of catalyst C in Example 9. The LHSV was 10 hr$^{-1}$ based on the flow rate of the combined feedstock and the total volume of catalysts C and A. The volume of catalyst A was 25% (by volume) of the total volume of catalysts C and A.

The experimental results from the tests in Examples 4–10 are summarized in Table 2.

TABLE 2

| Example | Catalyst(s) | Volume of Catalyst A (% of Total Catalyst Volume) | 2-Phenyl-Alkane Content of LAB (wt-% of LAB) |
|---|---|---|---|
| 4 | B | 0 | 26.2 |
| 5 | A at inlet, B at outlet | 15 | 34.3 |
| 6 | A and B mixed | 15 | 30.3 |
| 7A | E | 0 | 28.8 |
| 8 | A at inlet, D at outlet | 5 | 33.4 |
| 9 | C | 0 | 27.9 |
| 10 | C at inlet, A at outlet | 25 | 30 |

A comparison of Examples 4 and 5 shows that when 15% of the volume of a fluorided silica-alumina catalyst bed is replaced with a low-fluoride mordenite-containing catalyst at the inlet of the catalyst bed, the 2-phenyl-alkane content of the LAB increases by 8.1 percentage points. If that same volume of fluorided silica-alumina catalyst is instead commingled with the mordenite-containing catalyst throughout the catalyst bed, Example 6 shows that the 2-phenyl-alkane content of the LAB increases by 4.1 percentage points compared to Example 4.

A comparison of Examples 7A and 8, which takes into account the similar performance of catalysts D and E based on the prophetic Example 7B, shows that when 5% of the volume of a fluorided silica-alumina catalyst bed is replaced with a low-fluoride mordenite-containing catalyst at the inlet of the catalyst bed, the 2-phenyl-alkane content of the LAB increases by 4.6 percentage points.

A comparison of Examples 9 and 10 shows that when 25% of the volume of a fluorided silica-alumina catalyst bed is replaced with a low-fluoride mordenite-containing catalyst at the outlet of the catalyst bed, the 2-phenyl-alkane content of the LAB increases by 2.1 percentage points.

EXAMPLE 11

This example is prophetic and is based on actual pilot plant and commercial operations, on engineering calculations, and on experience with similar processes. A reactor is loaded with a cylindrical bed of fluorided silica-alumina catalyst prepared in the manner used in Example 3. Benzene and an olefinic feedstock containing olefins and paraffins and less than 0.2 wt-% coboiling aromatics are charged to the reactor. The reactor operates at alkylation conditions to produce LAB. The 2-phenyl-alkane content of the LAB is 28.8 wt-% based on the weight of LAB produced.

The reactor is reloaded with two cylindrical beds of catalyst. The first bed contains a volume of mordenite-containing catalyst prepared in the manner used in Example 1, and the second bed contains a fluorided silica-alumina catalyst prepared in the manner used in Example 3. The total volume of the two beds is the same as the volume of the single bed in the reactor prior to reloading. The volume of the first bed is 1% (by volume) of the total volume of the two beds.

Benzene and the same olefinic feedstock previously mentioned in this example are charged to the reactor at the same rate as before the reloading. The hydrocarbons contact the first bed first and then the second bed. The reactor operates at alkylation conditions to produce LAB. The 2-phenyl-alkane content of the LAB is 29.5 wt-% based on the weight of LAB produced.

EXAMPLE 12

This example is prophetic and is based on actual pilot plant and commercial operations, on engineering calculations, and on experience with similar processes.

Example 11 is repeated, except the volume of the first bed is 27% (by volume) of the total volume of the two beds and the 2-phenyl-alkane content of the LAB produced using the two beds is 40 wt-% based on the weight of LAB produced.

What is claimed is:

1. A process for producing linear alkylbenzenes, the process comprising:
    a) contacting benzene and an olefinic feedstock comprising a linear monoolefin having from about 8 to about 28 carbon atoms and having a concentration of coboiling aromatics of less than 2 wt-%, with a first catalyst comprising mordenite operating at first reaction conditions sufficient to alkylate benzene with the monoolefin and form linear phenyl-alkanes, wherein the first catalyst has a fluoride content of less than 0.05 wt-% based on the weight of the mordenite in the first catalyst, and recovering from the first reaction zone a first reaction product comprising linear phenyl-alkanes; and
    b) contacting at least a portion of the first reaction product with a second catalyst comprising silica-alumina operating at second reaction conditions sufficient to alkylate benzene with monoolefin, and recovering from the process a second reaction product comprising linear phenyl-alkanes, wherein the linear phenyl-alkanes in the second reaction product comprise linear 2-phenyl-alkanes and wherein the second reaction product has a concentration of linear 2-phenyl-alkanes of from about 25 to about 80 wt-% based on the linear phenyl-alkanes in the second reaction product.

2. The process of claim 1 wherein the first catalyst occupies a first volume, the second catalyst occupies a second volume, and the first volume is from about 1% to about 70% by volume of the sum of the first volume and the second volume.

3. The process of claim 2 wherein the first volume is from about 5% to about 15% by volume of the sum of the first volume and the second volume.

4. The process of claim 1 further characterized in that the mordenite has a framework silica:alumina molar ratio of from 12:1 to about 90:1.

5. The process of claim 1 further characterized in that the first reaction conditions comprise a pressure sufficient to maintain at least partial liquid phase or supercritical conditions and a temperature of from about 80 to about 200° C.

6. The process of claim 1 further characterized in that the first catalyst has a fluoride content of less than 0.01 wt-% based on the weight of the mordenite in the first catalyst.

7. The process of claim 1 wherein the second catalyst has an LOI of from about 1 wt-% to about 12 wt-%.

8. The process of claim 1 wherein the second catalyst has a fluoride content of from 1 to 6 wt-%.

9. The process of claim 1 wherein the second catalyst has a weight ratio of silica per alumina of from about 1:1 to about 19:1.

10. The process of claim 1 wherein the second catalyst comprises fluorided silica-alumina.

11. The process of claim 1 further characterized in that the second reaction conditions comprise a pressure sufficient to maintain at least partial liquid phase or supercritical conditions and a temperature of from about 80 to about 225° C.

12. The process of claim 1 further characterized in that the linear monoolefin contacts the second catalyst.

13. The process of claim 1 further characterized in that the first reaction product comprises the linear monoolefin.

14. The process of claim 1 further characterized in that no monoolefin contacts the second catalyst.

15. The process of claim 1 further characterized in that a reaction zone contains the first catalyst, wherein the recovering of the reaction product further comprises recovering from the reaction zone a first product stream comprising the reaction product, wherein the contacting of the reaction product with the second catalyst further comprises contacting a first aliquot portion of the first product stream with the second catalyst, and further characterized in that a second aliquot portion of the first product stream is recycled to the reaction zone.

16. The process of claim 1 further characterized in that a second reaction zone contains the second catalyst, wherein the recovering of the second reaction product further comprises recovering from the second reaction contacting zone a second product stream comprising the second reaction contacting product and recovering from the process the phenyl-alkanes in the second product stream in a first aliquot portion of the second product stream, and further characterized in that a second aliquot portion of the second product stream is recycled to the second catalyst.

17. The process of claim 16 further characterized in that a third aliquot portion of the second product stream is recycled to the first catalyst.

18. The process of claim 1 wherein the recovering of the first reaction product further comprises recovering a first product stream comprising the first reaction product, wherein the contacting of the first reaction product with the second catalyst further comprises contacting a first aliquot portion of the first product stream with the second catalyst, and further characterized in that the phenyl-alkane in the first product stream is recovered from the process in a second aliquot portion of the first product stream.

19. The process of claim 1 wherein the first catalyst and the second catalyst are in a common reaction vessel.

20. The process of claim 1 further characterized in that a paraffinic feedstock comprising a linear paraffin having from about 8 to about 28 carbon atoms is dehydrogenated in a dehydrogenation zone to dehydrogenate the linear paraffins and form a dehydrogenation product comprising the linear monoolefin and the coboiling aromatics, and the olefinic feedstock is formed from at least a portion of the paraffinic feedstock.

21. The process of claim 1 wherein the first catalyst is not treated with fluoride.

* * * * *